United States Patent [19]
Dziewulski et al.

[11] Patent Number: 5,135,853
[45] Date of Patent: * Aug. 4, 1992

[54] THREE COMPARTMENT BIOREACTOR AND METHOD OF USE

[75] Inventors: David Dziewulski; Marc S. Paller, both of Troy, N.Y.

[73] Assignee: Rensselaer Polytechnic Institute, Troy, N.Y.

[*] Notice: The portion of the term of this patent subsequent to Jan. 13, 2004 has been disclaimed.

[21] Appl. No.: 913,737

[22] Filed: Sep. 30, 1986

Related U.S. Application Data

[63] Continuation-in-part of Ser. No. 516,263, Jul. 22, 1983, abandoned.

[51] Int. Cl.⁵ .................. C12M 1/12; C12M 1/36; C12P 1/00
[52] U.S. Cl. ........................ 435/41; 435/243; 435/240.1; 435/240.241; 435/284; 435/288; 435/289; 435/311; 435/313; 435/315; 435/316; 435/813
[58] Field of Search .............. 435/41, 240.21, 240.23, 435/240.24, 240.241; 210/602, 615, 616

[56] References Cited

U.S. PATENT DOCUMENTS

| | | | |
|---|---|---|---|
| 2,958,517 | 11/1960 | Harker et al. | 435/286 |
| 3,186,917 | 6/1965 | Gerhardt et al. | 210/321.2 X |
| 3,463,615 | 8/1969 | Sochor | 55/36 X |
| 3,734,851 | 5/1973 | Matsumura | 210/632 |
| 3,856,475 | 12/1974 | Marx | 55/36 X |
| 3,883,393 | 5/1975 | Knazek et al. | 435/284 X |
| 3,926,561 | 12/1975 | Lucero | 436/178 |
| 4,062,771 | 12/1977 | Saupe | 210/34.2 X |
| 4,091,116 | 5/1978 | Edwards et al. | 435/288 X |
| 4,115,277 | 9/1978 | Swank | 210/489 X |
| 4,167,450 | 9/1979 | Chesbro et al. | 435/311 X |
| 4,178,209 | 12/1979 | Tolbert et al. | 435/286 X |
| 4,184,922 | 1/1980 | Knazek et al. | 435/283 X |
| 4,220,725 | 9/1980 | Knazek et al. | 435/240 X |
| 4,225,671 | 9/1980 | Puchinger et al. | 435/813 X |
| 4,241,187 | 12/1980 | White | 435/283 X |
| 4,306,521 | 12/1981 | Giles | 210/512.1 X |
| 4,443,544 | 4/1984 | Rogers et al. | 435/813 X |
| 4,636,473 | 1/1987 | Kleinstreuer | 435/311 X |
| 4,649,114 | 3/1987 | Miltenburger et al. | 435/284 X |
| 4,668,394 | 5/1987 | Badolato et al. | 210/489 X |

FOREIGN PATENT DOCUMENTS

| | | | |
|---|---|---|---|
| 3016490 | 11/1981 | Fed. Rep. of Germany | 435/287 |
| 0166985 | 10/1982 | Japan | 435/288 |

OTHER PUBLICATIONS

Perry et al. (ed.), Chemical Engineers Handbook, Fifth Edit, New York, McGraw-Hill, 1973, pp. 19-83.

Primary Examiner—Robert J. Warden
Assistant Examiner—William H. Beisner
Attorney, Agent, or Firm—McGlew & Tuttle

[57] ABSTRACT

A bioreactor includes three compartments. A middle compartment is meant to contain a biocatalyst and is separated from opposite end compartments by semipermeable membrane. The middle compartment is in the form of a vertically extending cylinder with domed top and bottom walls. The opposite end compartments are also in the form of domes but extend horizontally. Lower supply and upper discharge lines are connected to each of the end compartments. An agitator is connected in the bottom of the middle compartment and a degasser is connected to the top of the middle compartment.

5 Claims, 15 Drawing Sheets

THREE COMPARTMENT BIOREACTOR AND METHOD OF USE

CROSS REFERENCE TO RELATED APPLICATION

This is a continuation-in-part application for the inventors' previous application Ser. No. 516,263, filed Jul. 22, 1983, whose content is incorporated here by reference, and which is now abandoned.

FIELD AND BACKGROUND OF THE INVENTION

The present invention relates generally to bioreactor systems and in particular to a bioreactor system capable of continuous mode production.

The use of biocatalyst for the production of useful products has been a part of man's history for thousands of years. Until this century the production of useful products from biocatalysts was performed in batch-type reactors (fermenters) which for the most part use agitation as a means of intimately mixing the contents of the reactor and adding essential gases (i.e. oxygen, carbon dioxide, nitrogen, etc.) through some form of sparger. Furthermore, as man's basic knowledge of biological systems grew (i.e. pH, oxygen, sterility, nutrition, etc.), he began to utilize this information for the purpose of improving the quantity and quality of biologically derived products for commercial exploitation.

The basic economics behind biological production are two-fold: producing a product with greater value than the raw material it was derived from and producing a product that cannot be economically made in any other way, in both cases for the purpose of satisfying market demand.

For bulk biochemical production, such as beer, the principle costs are in the initial raw materials and initial capital costs for the production facility since millions of gallons of beer must be producted to obtain a reasonable return on the investment. It should also be noted that yields of these products are some of the highest of any biologically derived products.

At the other extreme is high-value biochemical production, such as monoclonal antibody, whose largest expense is in the downstream processing of the product. This occurs because of federal regulations stipulating the purity of the final product if it is to be used in vivo. In this situation, however, the very small amount of product produced and the difficulty in performing the production requires that the final product be sold at many orders of magnitude higher than the bulk biochemical for the same basic quantity.

Biochemical production is still today, for the most part, a batch operation. Many other industries such as oil and plastics have converted to continuous operation since continuous production typically requires much smaller capital investment to produce the same amount of product and one can either increase or decrease production to better meet market demand.

A number of bioreactor (fermentation) systems and processes have been invented for the purpose of bringing commercially usable, continuous production to the biologically-derived fermentation industry. To be a truly commercially-usable system, however, the system must substantially reduce the overall manufacturing and capital costs of the product to the producer at the same or higher yields since these are the producers incentives to make the investment in the system. A total overall manufacturing cost reduction related to the hardware can only occur by a continuous system that reduces both up-stream and down-stream unit operation costs and/or by increasing the overall yield of the system through regulating environmental and other parameters.

Another important consideration is the energy and mass conservation of the system. In a batch type of system, a considerable amount of energy and time is spent making the biocatalyst (mass). This is seen in the traditional batch growth curve during lag and log phase. Once the batch has been completed, however, the biocatalyst is then wasted. This usually coincides with stationary and/or death phase. Furthermore, when the up time and down time cycles of batch type systems are added into the equation as well as the tremendous loss in material should the system ever become contaminated, the real expense of batch systems in time, energy and mass becomes quite excessive. Almost all research into biocatalyts growth, behavior, and productivity has been done in batch systems since these were the only systems available. In recent publications it has been shown that biocatalyst can be maintained for many months without the loss of productivity. New continuous systems attempt to prolong stationary and/or maintenance phase for as long as possible, since the biocatalyst's life span, if handled correctly, can be extended to many months. If growth and productivity can be managed for long periods of time, then the initial energy and time required to create the biocatalyst (mass) becomes trivial over the length of a continuous system. However, unless the continuous system is able to manage growth and productivity without utilizing excessive resources, the continuous system would be as expensive as the batch system and offer no great advantage. Therefore, every unit operation of the continuous system must be optimized in such a way as to utilize the least amount of resource to obtain the desired results and still be able to manage the growth and productivity of the biocatalyst. As used here, the term biocatalyst or mass will be understood by the skilled artisan in this field to include enzymes, cells or other biochemical catalyst.

Prior to the present invention, the prior art relating to this invention may be classified into two major hardware system catagories, which are recycle and immobilization. None of the prior art integrates into its hardware or process, capabilities or those important characteristics mentioned above.

A recycle system typically consists of a standard batch bioreactor which may be stirred and/or contains a sparging device and where the biocatalyst and other contents are pumped out of the reactor and then through some form of separator (i.e. membrane, centrifuge, dialysis, etc.) for the purpose of separating the product from the biocatalyst. What remains after the product has been separated is then pumped back into the reactor to be reused. The obvious intent is to reduce downstream processing costs by incorporating the separation step as part of the fermenter. The advantages to this type of system include the ability to agitate and aerate the biocatalyst directly for better mass transfer, separation of the product (if it is extracellular), and ease of monitoring the environment of the biocatalyst. The disadvantages are:

1. Pumping the biocatalysts can damage or destroy them and thereby nullify the benefits obtained from the built-in separation step by adding additional components to the product stream, releasing protieolytic enzymes from a biocatalyst that would damage or destroy the remaining biocatalyst, and where membranes are used, fouling would occur faster. Monitoring probes would also foul faster with the addition of further debris. This would also greatly increase downstream process costs in high-value biochemical production to reach the required purity levels.

2. The probability of contamination of the biocatalysts by having to sterilize and move the biocatalyst through additional is increased.

One example of a recycle system utilizing dialysis for separation is that of U.S. Pat. No. 3,186,917 issued Jun. 1, 1965 to Gerhardt et al. In one configuration, Gerhardt et al utilize a standard fermenter whose contents are circulated through the right-end compartment of a three compartment chamber by pumping. The compartments are separated by dialysis membranes. Dialysate is circulated through the middle compartment while feed circulates through the left-side compartment both by pumping. By regulating the flow of the various recycling fluids, product is extracted by the dialysis and feed passes through the dialysis compartment into the recycling biocatalysts fluid. Gerhardt et al controls the product production and product extraction by the volume of dialysis fluid and the rate at which it is circulated.

One other illustration of a recycle system is Japanese patent 57-166985 of Oct. 14, 1982 to Kenkyusho. In his system, Kenkyusho uses the same approach as Gerhardt et al even down to the same three compartment chamber. The structural differences are that Kenkyuso uses two chambers which are interconnected and in place of dialysis membranes, microporous membranes are used instead. Kenkyusho recycles the biocatalyst through the middle compartment and sends the other liquid through one-side of the first chamber and exits through the other side of the chamber to enter the second chamber where the same thing occurs. The product is separated by recycling the separated product stream back through the recycling biocatalyst stream. Aeration, agitation and monitoring all occur within a standard batch fermenter used to hold the biocatalyst.

Both of these systems utilize a standard batch fermenter with extra tubing to make the systems continuous. Yet both these systems designs lack the ability to easily control the biocatalysts growth and activity.

An immobilized system typically consists of a biocatalyst that is immobilized onto a stationary surface. In an immobilized system, the biocatalyst cannot be directly moved and is not moved nor generally, is direct aeration applied to the biocatalyst. The stationary surface could be a membrane, sheet of plastic, or even a sheet of glass. The basis of an immobilized system is to utilize diffusion as the means of bringing and removing material to and from the biocatalyst, attempt to duplicate the cardio-vascular system, and to separate the biocatalyst from the product. Typically, a large reservoir holds the circulation fluid. It is in this reservoir that aeration would take place by some other device, but not where the biocatalyst is located and where the environmental variables are measured. The circulation fluid is either very slowly passed over the biocatalyst or flows on the other side of a membrane holding the biocatalyst. These systems are generally called perfusion reactors. This is because they rely on diffusion and act as a plug-flow reactor as the fluid travels over the biocatalyst or membrane by increasing in wastes and decreasing in nutrients. Instead of constantly circulating the biocatalyst as with recycle, the immobolized system constantly circulates the feed past the biocatalyst. These types of systems are generally much simpler and require less capital investment. The advantages of this system are that shear sensitive biocatalyst and slow growing biocatalysts can be easily grown. Also, as anchor dependent biocatalysts, are simple to set up and operate. This system can also easily be computer controlled/automated, and separation is possible.

The disadvantages of this system are:
1. Inability to directly agitate or aerate the biocatalyst;
2. Inability to directly monitor and, in some cases, even visibly see the biocatalyst;
3. Inability to control the growth and activity of the biocatalyst;
4. Seeding the reactor;
5. Many scale-up problems; and
6. Sterilizability, since most units are completely made of plastic.

An example of an immobilized perfusion system is U.S. Pat. 3,734,851 issued May 22, 1973 to Matsumura. In his system, Matsumura entraps biocatalysts between two dialysis membrane sheets, forming a membrane bag. Feed is circulated over the one side of the membrane bag while another stream circulates on the other side of the bag. The biocatalyst is immobilized (entrapped) within this membrane bag. There is no agitation nor direct aeration possible for the contents of the bag nor can the biocatalyst be directly monitored or visibly seen. A number of these bags are placed on top of one another with appropriate channels between them.

Recycle and immobilization systems both have certain advantages and capabilities inherent in their respective design. The advantages of one however, are for the most part, the disadvantages of the other.

SUMMARY OF THE INVENTION

The primary objective of the present invention is to provide the biologically-derived product industry with a commercially usable, microprocessor controlled, fully automated, continuous bioreactor system and method that has the versatility and capability to produce a wide array of products utilizing various biocatalysts, more efficiently and without the disadvantages and problems inherent in the other two continuous production methods cited above and with capabilities unavailable before in bioreactor systems. Such a bioreactor and method reduces both the costs of downstream and upstream processing, requires low capital investment, and achieves a substantial manufacturing cost reduction.

The above and other objects are achieved by the present invention by providing a bioreactor production system which, in its simplest form, consists of a three compartment bioreactor, a reservoir, apparatus for aeration, apparatus for degassing, appropriate hardware devices for creating and maintaining fluid dynamics within the entire system, and appropriate hydraulic items such as, but not limited to tubing, piping, assorted valves, and fittings, and all of which is controlled by a microprocessor. These items should be made from materials which have undergone toxicity testing, are capable of being sterilized, and can withstand a laboratory or industrial environment (i.e. 3162 stainless steel, teflon, glass, etc.).

A further object of the invention is to provide a bioreactor which is simple in design, rugged in construction, economical to manufacture, and easy to operate and maintain.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
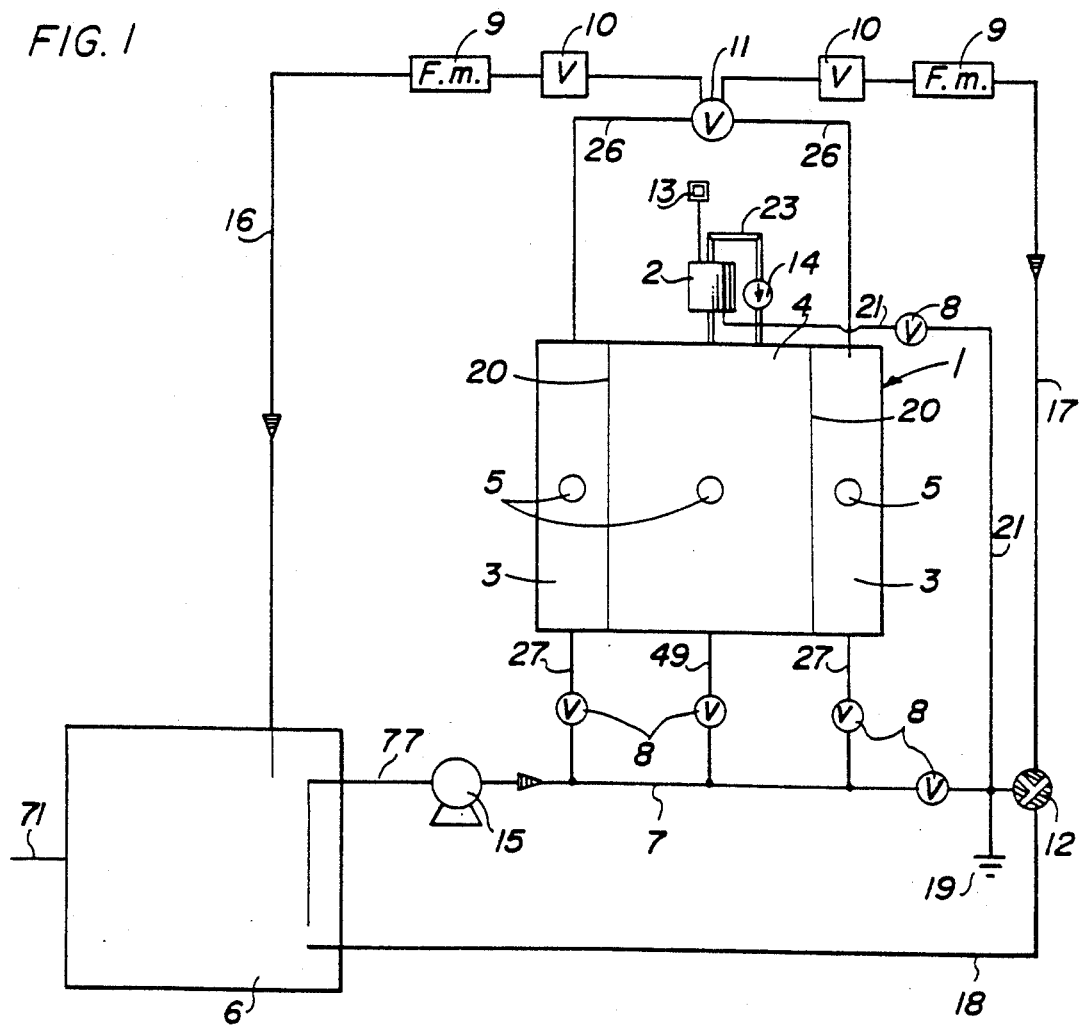
FIG. 1. is a schematic diagram illustrating the fluid circuit for use with the bioreactor of the present invention.

Referring to the drawings in particular, the invention embodied therein comprises a bioreactor which includes a middle compartment and two opposite end compartments which are separated from the middle compartment by a semipermeable membrane, the middle compartment used to contain a biocatalyst and the end compartments being used to supply fluid to and tap product from the middle compartment, through the semipermeable membranes.

Figure 2:
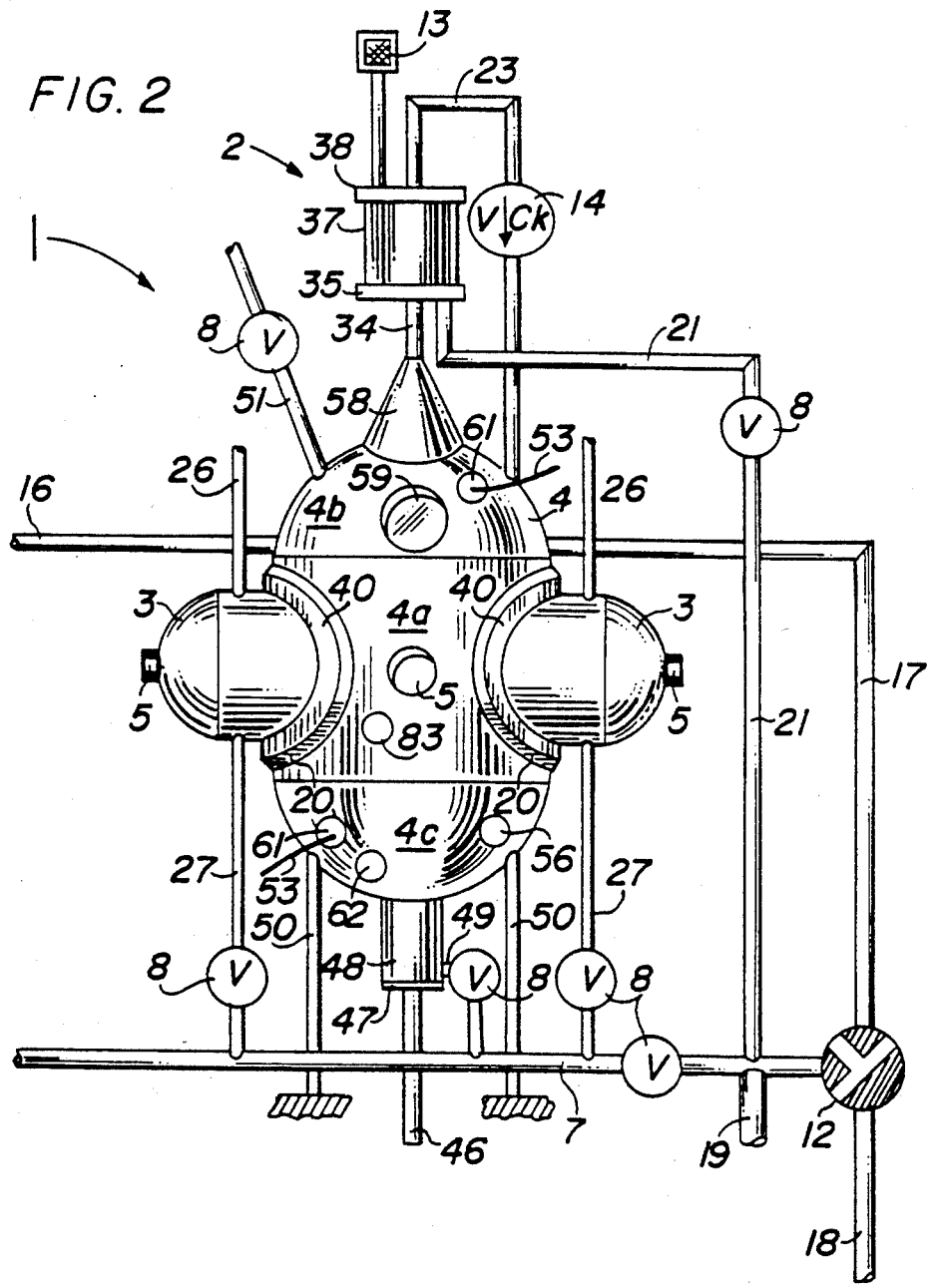
FIG. 2 is a side elevational view showing one embodiment of the reactor according to the present invention with its manifold and other connected tubing.
Figure 3:
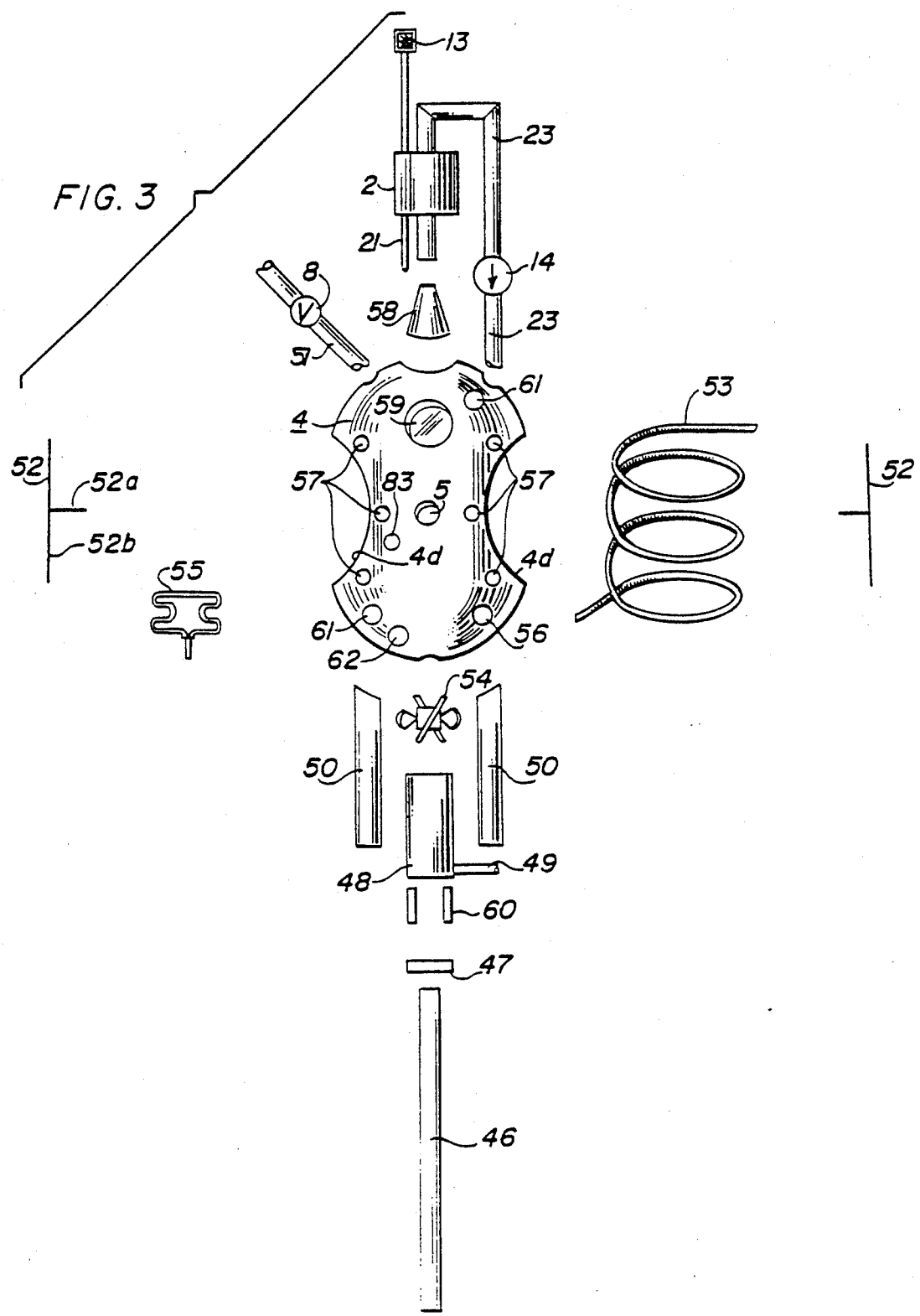
FIG. 3 is an exploded side view of the middle compartment of the reactor shown in FIG. 2, showing struts, means for attachment, agitation, aeration, temperatue control, pressure measurement, sampling lines, seeding lines, feed lines and degasser.

The reactor generally designated 1 in FIGS. 1, 2 and 3, comprises three separate compartments 3,4 and 3. The middle compartment 4, which typically houses the biocatalysts, consists of a vertical hollow cylinder 4a of appropriate material and dimension, having a dome 4b protruding outwardly from the top and a dome 4c protruding outward from the bottom of the cylinder such that the entire shape resembles a capsule. A hole 4d penetrates horizontally and directly through each side of the vertical portion of the capsule. The center of those holes are half way between the capsule's top and bottom. The diameter of the holes are smaller than either that diameter which would cause the capsule to be cut in half, or that diameter which would cause the holes to penetrate the curved portion of the capsule's domed top or bottom. Located on the outside of each hole of the capsule are means of attaching the end compartments 3,3 to the middle compartment 4 with a membrane packet 20 in between the two end compartments and the middle compartment. A supporting cross-shaped strut 52 whose horizontal member 52a is curved and follows the horizontal circumference of the capsule and whose vertical member 52b runs parallel with the vertical portion of the capsule, is mounted in each hole, whereby the intersection of both strut members is the centerline of the hole 4d. The capsule is further modified with the addition of tubing to optimize the operation for filling, seeding, aerating, sampling and emptying the capsule. The invention also includes an appropriate means for monitoring/controlling the internal temperature and environmental conditions, an appropriate means for monitoring pressure, an appropriate means of agitation, a degassing unit, and appropriate means for viewing inside the capsule, all of which may be necessary for the purpose of producing a product from a particular biocatalyst. Details of these features are discussed later.

Figure 4:
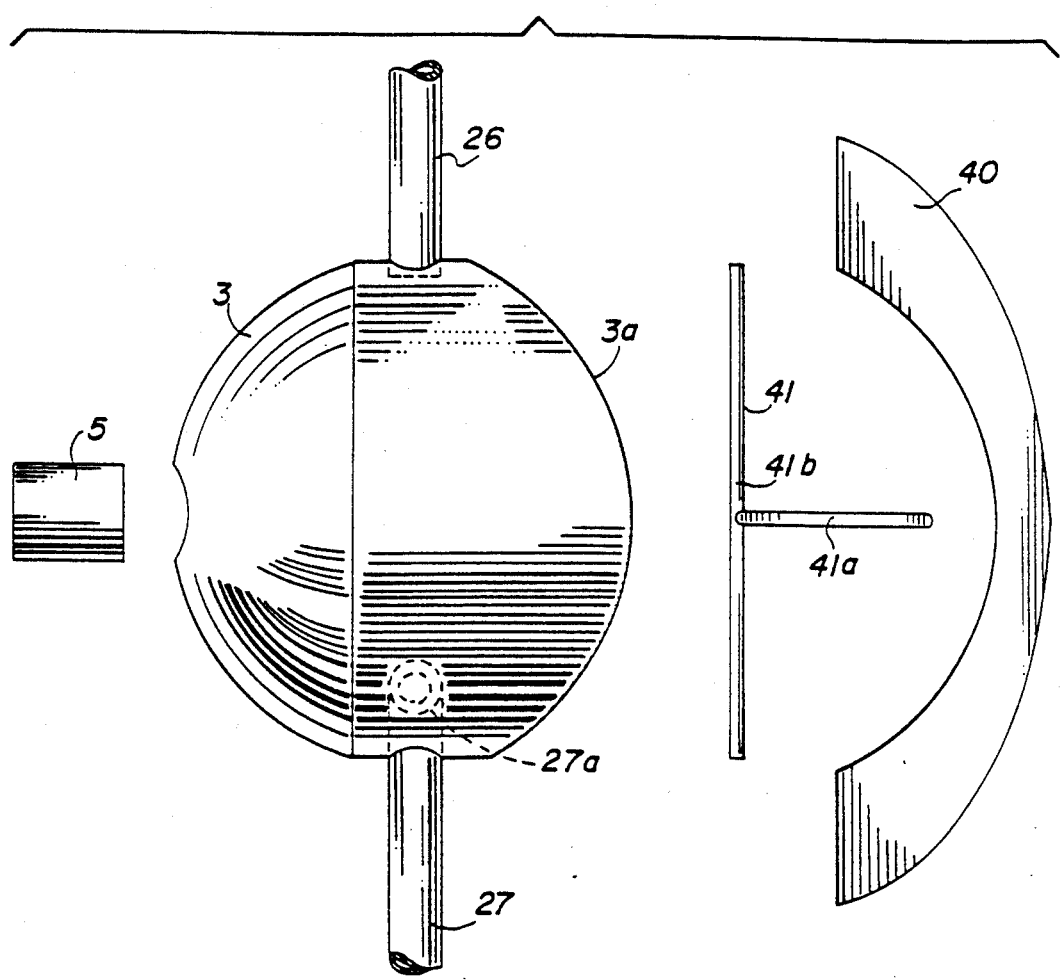
FIG. 4 is an exploded view of the domed end component of the reactor in FIG. 1 showing struts, feed lines and means for pressure monitoring.

The two end compartments 3,3 each comprise hollow cylinders (FIGS. 2 and 4) whose inner diameters are the same as the hole 4d in the middle compartment 4, and where one side is domed while the other side is opened. The opened side 3a is cut to follow the circumference of the middle compartment 4 plus the thickness added for the membrane packet 20 so that it will mate to the middle compartment 4. Each opened side 3a has means of attaching the end compartments to the middle compartment with a membrane packet 20 in between, whereby the centerline of the hollow horizontal cylinder is the same as the centerline for the hole it is to be mated with in the middle compartment. Each opened side also contains support struts 41, whose horizontal component 41a is curved and follows the circumference of the middle compartment plus the added thickness of the membrane packet, whose vertical component 41b runs parallel to the vertical cylinder of the capsule, and whose intersection of both the horizontal and vertical components is the center line for the horizontal cylinder and the hole through the capsule. The ends of struts 52 and 41 are connected to the respective compartments 4 and 3 by welding bonding or other means. The struts 52 and 41 are, in the assembled state, spaced from each other in each hole 4d by the thickness of a packet 20 to hold the packet in a curved state between compartments 3 and 4.

Each end compartment 3 contains two vertical tubes 26 and 27 where one tube penetrates the top and the other tube penetrates the bottom of the horizontal cylinder. The bottom tube 27 which penetrates for a small distance inside the horizontal cylinder has a bent end 27a bent at an angle inside the horizontal cylinder, perpendicularly to the vertical plane of the centerline which passes through the hole in the vertical cylinder of the capsule so that a vortex, which creates tangential motion around the membrane packet, may be formed when fluid is pumped into either end compartment. Each end compartment also has means for measuring at least the pressure and/or other physical or chemical parameters inside the compartment. This is shown as a pressure transducer 5 for each compartment 3, 4, 3.

Figure 8:
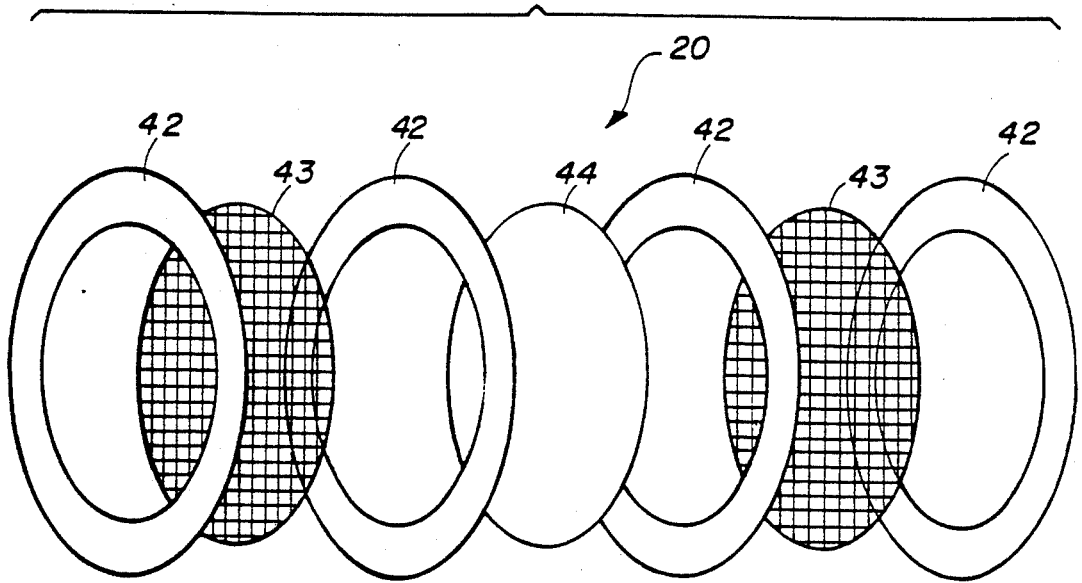
FIG. 8 is an exploded view of the membrane packet of FIG. 2 showing the screens, sealing material and semipermeable membrane.

The two end compartments 3 are separated from the middle compartment 4 by the compatible membrane packet 20 shown in FIGS. 2 and 8 which consists of a membrane 44 that is placed between two support screens 43, 43. The purpose of placing the membranes 44 on either side of the middle compartment is to hold the biocatalyst within the middle compartment. Furthermore, the packet 20 also serves as the seal between the middle compartment 4 and the end compartments 3. The packet 20 is formed by sealing the membrane 44 and support screens 43 betwen pieces of suitable sealing material 42 whose center has been cut out to match the diameter of the hole 4d in the middle compartment 4 and the sealing material's outer diameter has been cut to yield a sufficient outer diameter for sealing the respective end compartments 3, the support screens 43 and the membrane 44. The sealing material 42 must be of a material that is flexible, durable, nontoxic, sterilizable and be able to seal around the screens and membrane at various pressures (e.g. PTFE or silicone). The membranes 44 should be of a type that can be easily sterilized, will not adsorbing considerable amounts of material, and will permit the easy transport of material through the pores without causing considerable backpressure. Each membrane of different chemistry and structure has its characteristic properties regarding preferential passage of certain molecules, permitted flow rate, toxicity and ease of handling, strength, durability in-use, etc., as is well-known in this art and is selected accordingly, by one skilled in the art. Each compartment 3 has a lip 40 attached at its opened side 3a by welding bonding or the like. Lip 40 is curved so that it can hold the outer periphery of packet 20 against compartment 4. Lip 40, and thus compartment 3 is connected to compartment 4 by toggle bolts threaded bolts chips, clamps or the like which are shown schematically 57 in FIG. 3.

Once the reactor is assembled, the middle compartment is separated from the two end compartments 3 by the membrane packets 20 which are mechanically supported in place by the struts. The reactor's final shape was selected, based on mixing studies, which showed that there were no dead spaces in the middle compartment 4, that a vortex could be achieved in the end compartments as well as for the purpose of filling and completely draining the middle and end compartments, and for the purpose of easy assembly or disassembly and for maintenance of the hardware.

Figure 9:
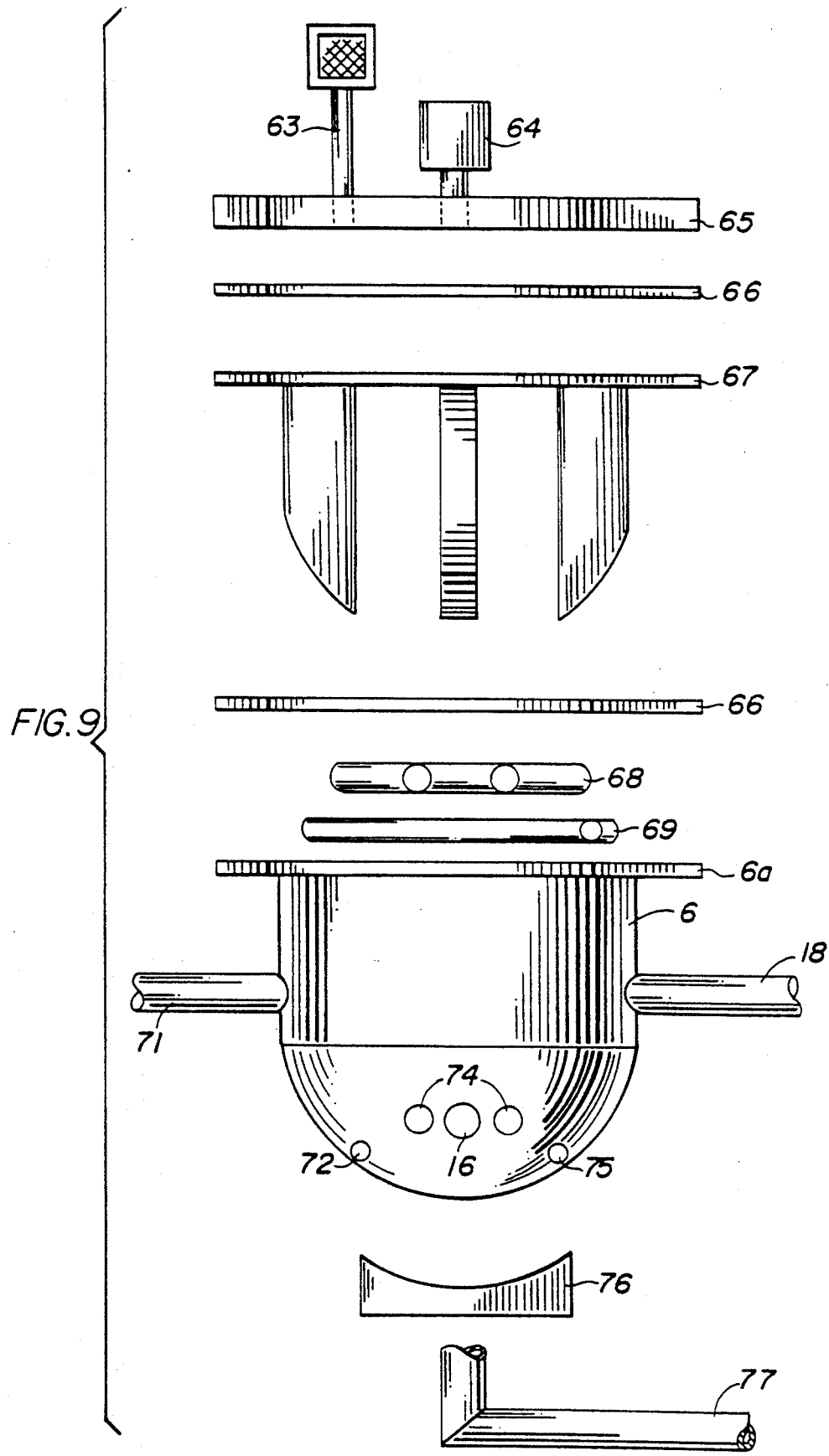
FIG. 9 is an exploded side view of the reservoir of FIG. 1 showing means for aeration, temperature control, sampling lines, a vent and other hydraulic lines.

The reservoir 6 shown in FIGS. 1 and 9 is required for holding the fluid that is circulated through a manifold 7 to one of the two compartments 3 of the reactor 1 and then recycled back to the reservoir 6 from the same side compartment, altering the chemical composition of the fluid that is sent to the reactor by the addition of gases or solutions, and reconditioning spent media that is recycled back to the reservoir after being processed through the reactor. The reservoir 6 consists of a sealed vessel of appropriate size and compatible material which has been modified to permit the optimized abilities of aeration of the fluid, the venting of gases, appropriate input and output hydraulic lines, appropriate monitoring of the fluid composition and temperature, an appropriate means for mixing the contents of the reservoir, and appropriate temperature control.

As shown in FIG. 9, reservoir 6 has an upper open top with a flange 6a which can be bolted or otherwise connected to a reservoir lid 65. Two gaskets of sealing material 66, 66 sandwich the flange of an insertable baffle 67 which facilitates mixing of the contents of reservoir 6. The baffle 67 has fixed vanes which extend down into the interior of the reservoir and against which fluid moves as it enters and leaves the reservoir for mixing fluid. Temperature control is achieved using a heatable temperature control coil 68 which has, for example, a resistive heating wire that can enter and leave the interior of the reservoir through input and output openings 74, 74. The coil 68 sits near the bottom of the reservoir near an entry port for an unspent fluid recycle line 16 which is also shown in FIG. 1.

Spent fluid recycle line 18 penetrates the reservoir 6 near its middle level as does a fluid input 71 for admitting fluid into reservoir 6. Reservoir lid 65 carries a reservoir vent 63 with a filter on the top for discharging gases from the top of the reservoir. A level controller 64 is also connected to the lid 65 for measuring the level of liquid in the reservoir and starting or stopping pump 15 and heater 68 if the level rises too high or falls too low. Controller 64 can also be connected to a secondary pump for filling the reservoir or for liquid make-up. Controller 64 is of known design.

An aerator 69 in the form of a semipermeable or porous tube, is also fitted near the bottom of the reservoir 60 and receives gas for aeration through opening 75. A sampling port 72 is also provided near the bottom of the reservoir which is normally capped but which can be opened to tap a sample of fluid from the reservoir.

Figure 10:
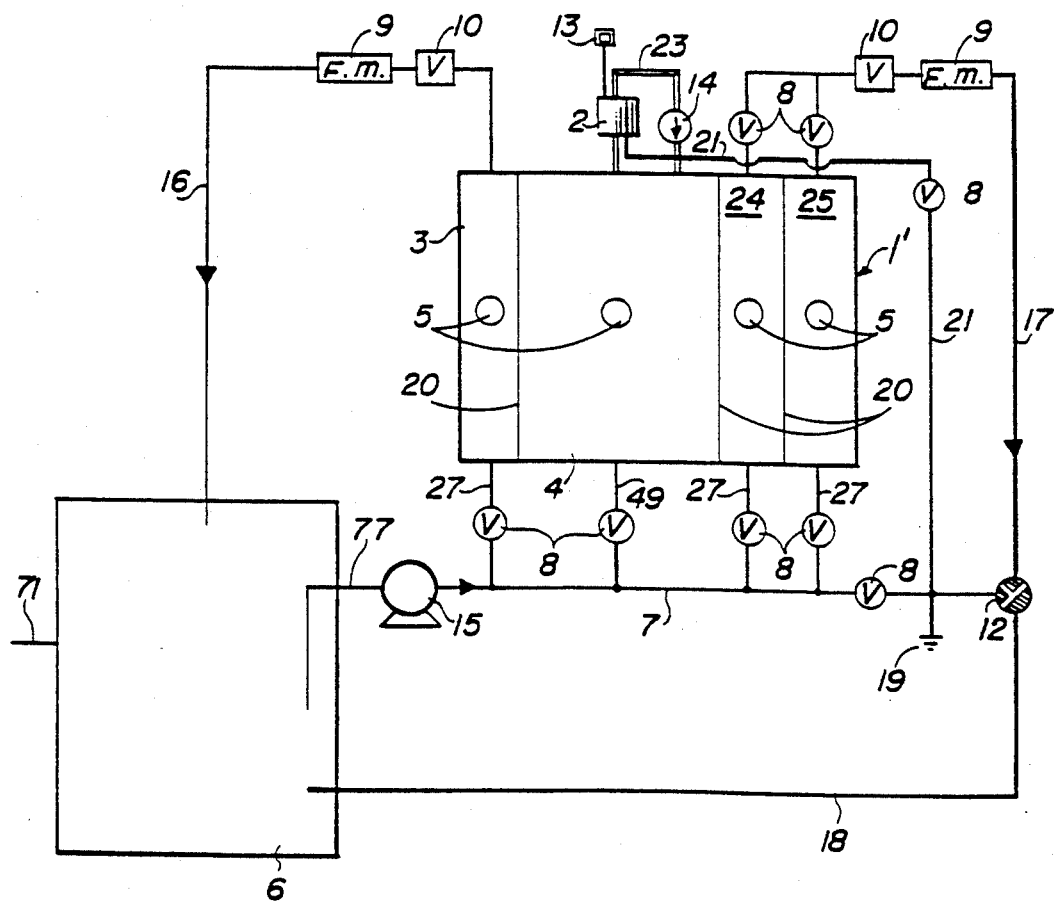
FIG. 10 is a view similar to FIG. 1 showing a hydraulic circuit with an embodiment of the invention having an intermediate compartment with modified domes and compartments.

The reservoir 6 sits on a reservoir base 76. A fluid outlet 77 is connected to the bottom of the reservoir as shown in FIG. 1 and 10 outlet 77 is also connected to a supply 15 to supply pump fluid from reservoir 6 to the manifold 7.

It is noted that throughout the figures the same reference numeral is used to designate the same, similar or equivalent parts.

A manifold 7 is required, where one end is connected to the reservoir 6 and the other end to a waste line 19 and container, with appropriate valving 8 and tubing 16, 17, 18 and 21 for the purpose of redirecting the liquid in the system so that the operations of filling, emptying, backwashing, washing and collection of product from the respective reactor compartments and for the added purpose of emptying the reservoir, can easily occur.

The aeration apparatus 69 in FIG. 9 and 55 in FIG. 3, is required for the purpose of supplying the necessary gases to the biocatalyst, and/or to one of the three compartments in such a manner as to produce bubbles whose diameter is sufficiently small as to deliver the maximum mass transfer of gas to the liquid per bubble with minimum added agitation, if any, and to reduce the shearing effects of large bubbles in appropriate applications of the hardware. This is due to the increase in surface area to volume ratio, the increase in bubble number, and the increase in residence/contact time of the bubble with the solution. An aerator may be placed inside appropriate compartments of the reactor and/or inside the reservoir. The aerator consists of a hydrophobic membrane tube of appropriate length and diameter to yield a sufficient range of gas flow rates, and of appropriate pore size for the purpose of producing bubbles of a diameter and quantity for maximum mass transfer of the gas to the liquid. A ridge support structure is used to shape and anchor the hydrophobic membrane tube for maximizing the delivery of the gas throughout the volume of the liquid. Both ends of the tube are connected to a gas source.

Figure 12:
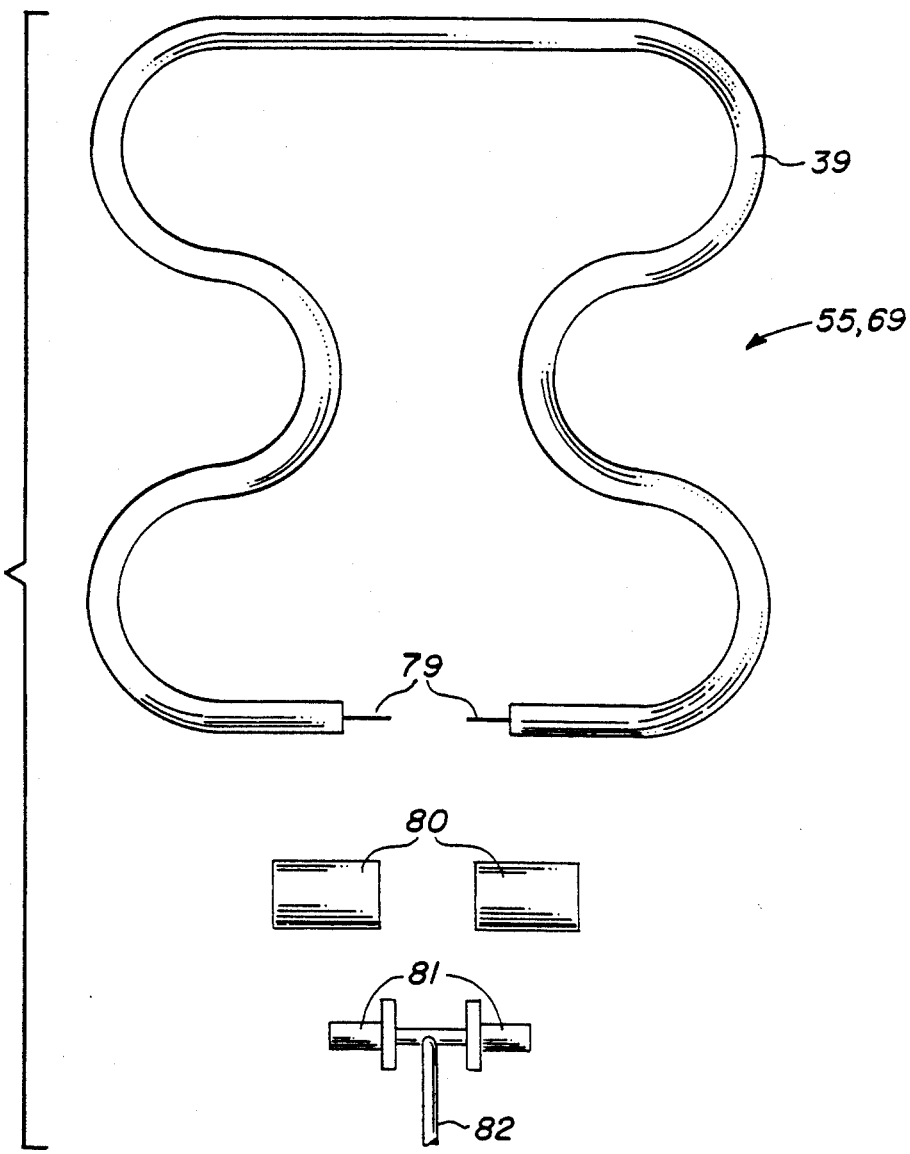
FIG. 12 is an exploded view showing the aerator and associated parts which can be used in the reservoir of FIG. 9 as well as in the middle compartments of FIGS. 2,3 and 11.

Both the aerator 55 for the bottom of the middle compartment 4 and the aerator 69 for the bottom of the reservoir 6 are shown in greater detail in FIG. 12. The hydrophobic hollow membrane tube 39 contains a wire support 79 that runs through the inside of the tube to form a substantially rigid shape seen in FIG. 12. Both ends of the tubes are connected through holders 80 to tubing inserts 81 and thereafter to a T-connection 82 acting as an aerator input for supplying appropriate gases into the ends of tube 39. The holders 80 may be fastened to the wall of either the middle compartment 4 or the reservoir 6 to hold the tube 39 in place. An hourglass shape is shown in FIG. 12 and exemplifies an advantageous shape, which while lying horizontally near the bottom of the appropriate reservoir or compartment, provides an advantageous pattern of rising bubbles in the fluid. An example of the material that can be used as hydrophobic hollow membrane tube 39 is PTFE (supplied by the W. L. Gore Company).

Figure 7:
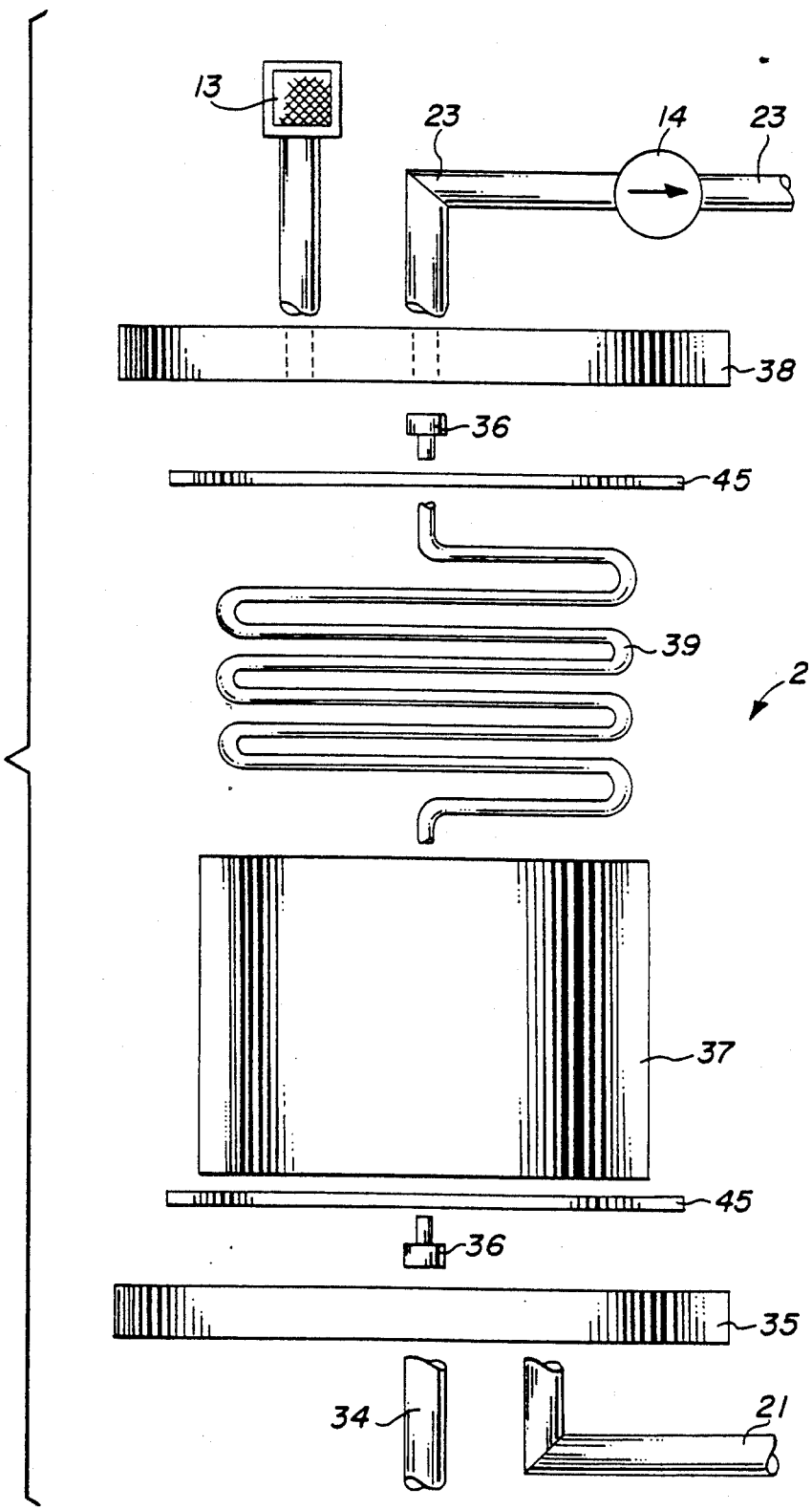
FIG. 7 is an exploded view of the degasser unit of FIG. 1, showing the coiling of a membrane, and the connection of the membrane to tubing.

It is noted that the same type of hydrophobic hollow membrane tube 39 can be used in a degassing unit of the invention shown in FIG. 7.

Figure 11:
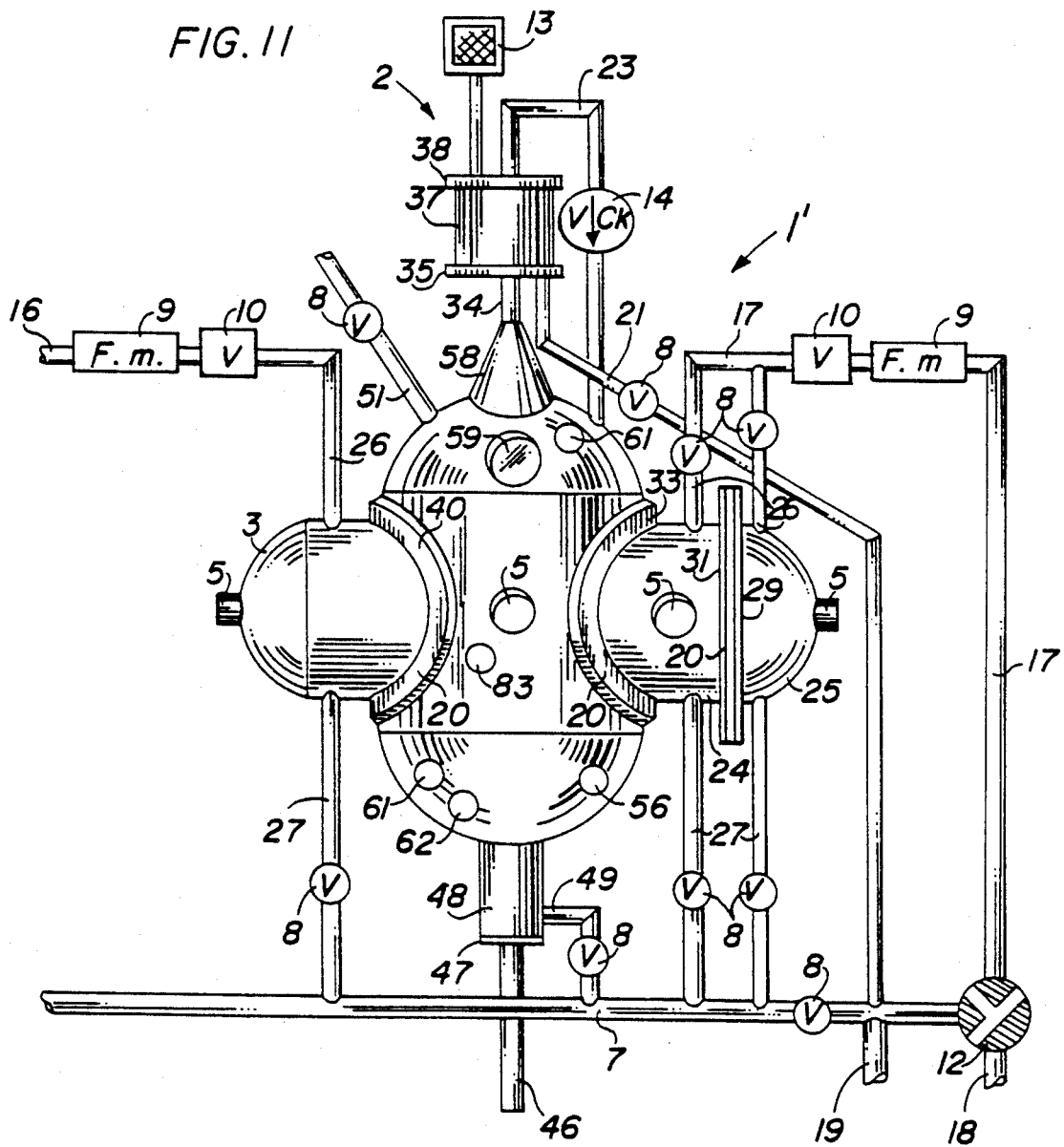
FIG. 11 is a view similar to FIG. 2 showing the reactor of FIG. 10.

The special degassing unit 2 shown in FIGS. 1, 2, 3, 7, 10 and 11, is required for removing gasses that have been added to a specific compartment during operation of the reactor since there is no headspace present in the reaction. (i.e. the reactor is completely filled with fluid). The unit separates the gas from the liquid sending the liquid back over line 23 and check valve 14 to the reactor and the gas out to the atmosphere through vent 13, thereby eliminating any foaming problems. The degassing unit is mounted on the top of the biocatalyst compartment 4 or any other appropriate compartment, and consists of two parallel plates 35 and 38 separated by a hollow cylinder 37 with two tubes (23 and the tube for vent 13) penetrating the top plate and two tubes (21, 34) penetrating the bottom plate into the internal volume of the cylinder. Clamping the two plates 35, 38 together seals the internal volume of the cylinder 37. One top tube 23, which has the check valve 14 in line, reenters the top of the compartment 14 that the unit is mounted on, while the other top tube goes to the gas filtering and venting device 13. Inside the cylinder is another hydrophobic membrane tube 39 which is appropriately coiled and one end of the membrane tube is connected to the top plate tube 23 at an insert 36. The other end of the membrane tube 39 is connected to the bottom plate at another insert 36 and to the tube 34 that is also directly connected to the reactor for the purpose of forming a continuous hydraulic pathway. The other bottom tube 21 serves as a drain and has appropriate valving and tubing (FIGS. 1 and 11). Sealing material 45 seals plates 35 and 38 to cylinder 37 to close the interior which contains the tube 39. Gas in the top of compartment 4 (or any other compartment outfitted with the degasser) enters tube 39 along with fluid from the top of the compartment. The gas then passes through the wall of tube 39 into the space around the tube in cylinder 37. This gas then leaves cylinder 37 over vent 13. The entrained fluid returns to the compartment over line 23 and check valve 14. Any fluid that passes through the wall of tube 39 into cylinder 37 is drained through line 21, one valve 8 (FIG. 2) and drain line 19.

Figure 5:
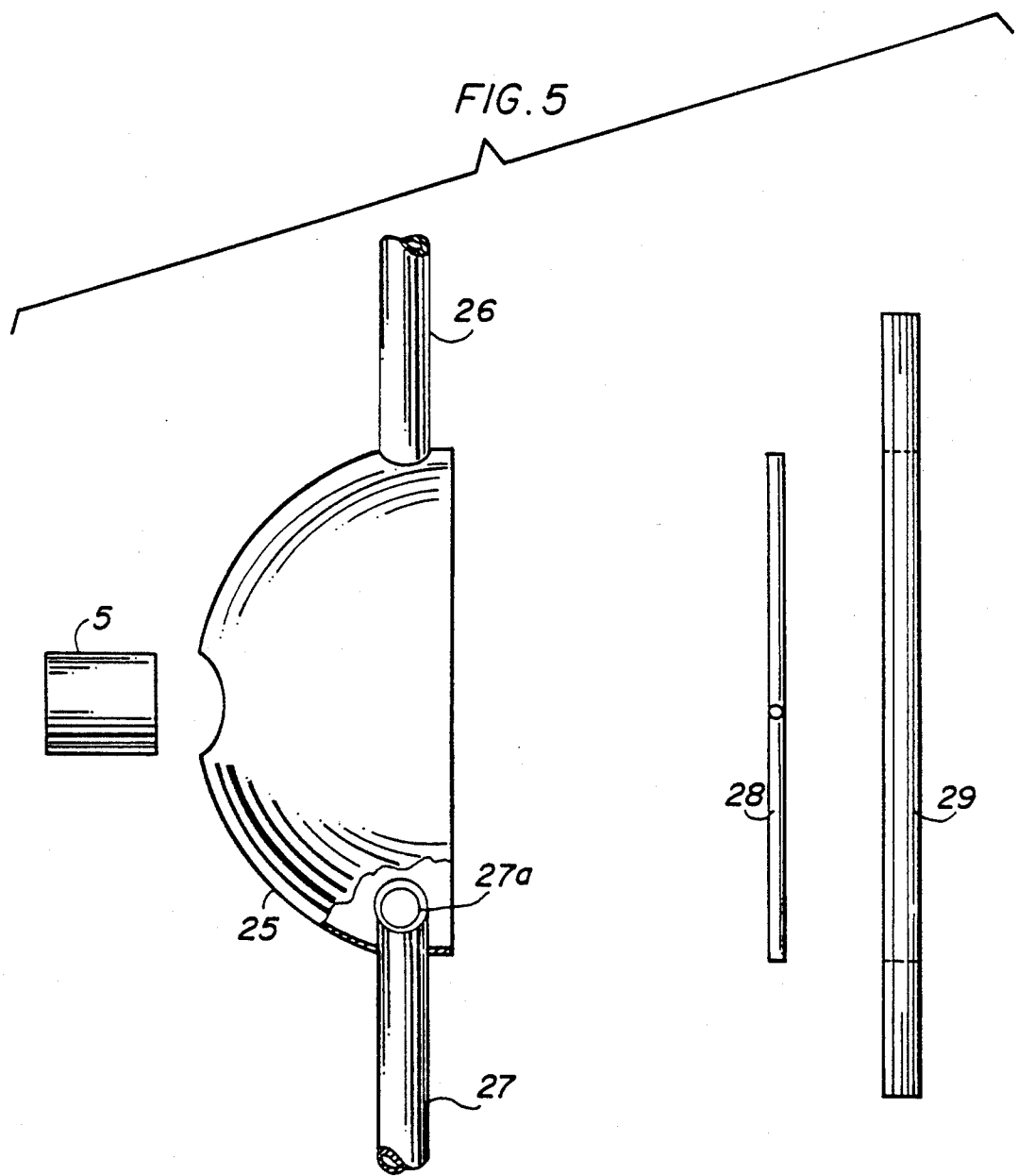
FIG. 5 is an exploded view similar to FIG. 4 but showing an alternate embodiment of the domed end compartment.

In place of one or both end compartments 3, the domed end of an end compartment may be left opened resulting in an opened end which resembles a hollow horizontal cylinder 24 (FIG. 6) of a appropriate length. This new intermediate compartment, containing struts 31 and 32 may be mated and attached to a modified domed end compartment 25 (FIG. 5) with an additional membrane packet in between and the other end of the intermediate compartment has the ability to attach to the middle compartment 4 with membrane packet in between, or may be mated to another intermediate compartment with or without a membrane packet in between. This could lead to another middle compartment, thereby connecting two reactors together. When mated to a domed end compartment, a modification to the domed end compartment would be necessary. The opened end of the domed end compartment would resemble a hollow horizontal cylinder with the same inner diameter as the compartment it was being mated to for the purpose of concentrating the desired product inside the reactor for the later product collection by use of an ultrafiltration membrane packet in between the intermediate compartment and the modified domed end compartment, which are attached together.

The purpose of mating two intermediate compartments is to permit attaching different middle compartments together. This new compartment would also contain a bottom tube and top tube that penetrates the compartment for the purpose of filling and emptying the compartment as well as the bottom tube extending into the compartment and bent perpendicular to the centerline of its hollow circular center for the purpose of creating tangential motion should liquid need be pumped into that particular compartment for backwashing, or product collection. Each of these compartments also has a means for measuring at least the pressure and/or other physiochemical parameters inside the compartment.

Turning once more to FIGS. 5 and 6, the modified end compartment 25 includes a lower tube 27 having a perpendicularly bent end 27a to produce the tangential flow effect mentioned above. The upper tube 26 extends through the upper end of compartment 25. The strut 28 is cross-shaped and planer and is fixed in the opening of compartment 25 by welding, bonding or other suitable means. A pressure transducer 5 is fitted in the end of compartment 25. A wide lip 29 is attached, for example by welding or bonding, to the outer edge of modified end compartment 25 near its open side. Lip 29 is flat and has an inside opening which corresponds to the outside diameter of the compartment 25.

Figure 6:
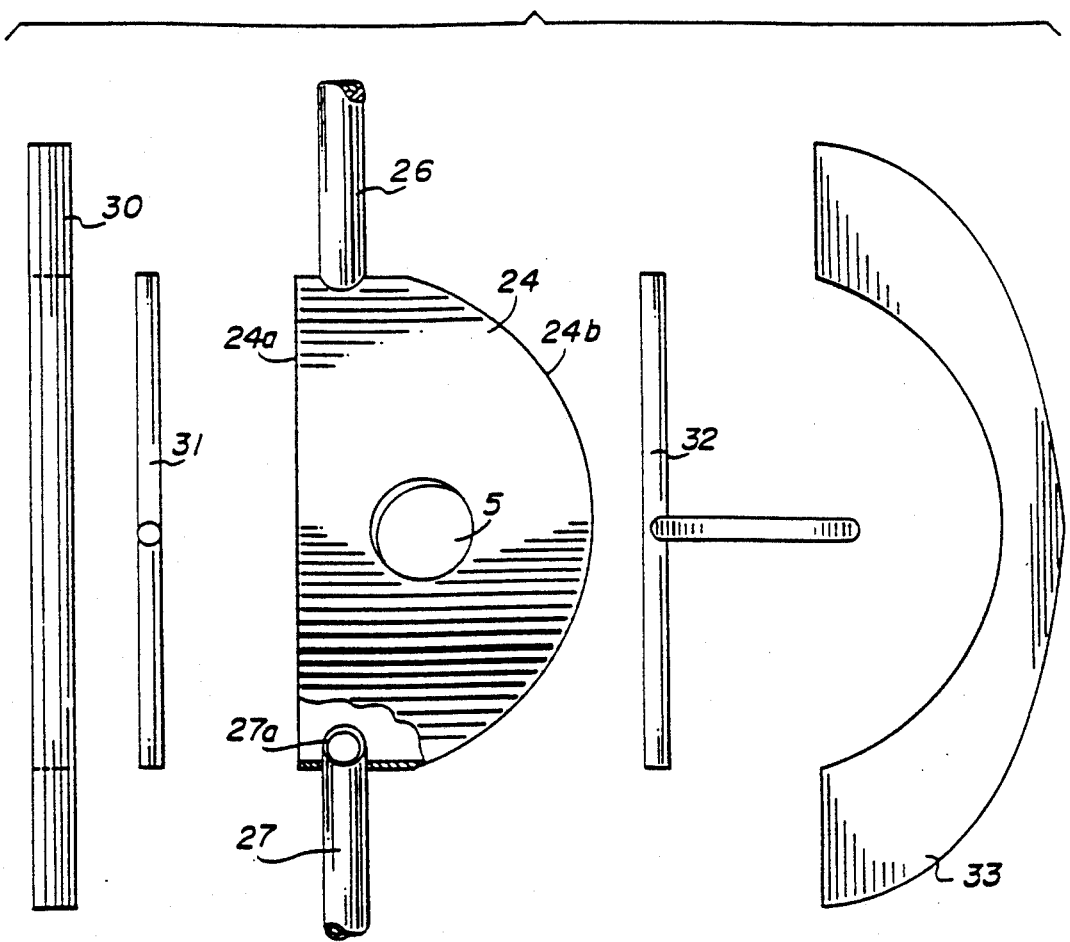
FIG. 6 is an exploded view similar to FIG. 4 showing an intermediate compartment which can be used in accordance with the present invention.

As shown in FIG. 6, the intermediate compartment 24 carries a pressure transducer 5 at its side and also has bottom tube 27 with a bent end 27a. A cross-shaped strut 31 is fixed in the open end 24a of the intermediate compartment 24 and a strut 32 which is formed similarly to the struts 41 and 52 of compartments 3 and 4, is connected into the opposite open end 24b of intermediate compartment 24. A curved lip 33 which is similar to curved lip 40 is bonded around opening 24b and a flat lip 30 is connected around opening 24a. A packet 20 can be clamped by clamps, bolts or other appropriate means between lips 29 and 30. This packet is held firmly between struts 28 and 31. Another packet can be held between strut 32 and a similarly shaped strut in the middle compartment. While the packet between struts 29 and 31 is held flat, the packet between strut 31 and the strut in the middle compartment is curved to follow the outer contour of the middle compartment.

FIG. 11 shows an embodiment of the invention where one of the end compartments 3 is replaced by the modified end compartment 25 and intermediate compartment 24. Tubes 26 and 27, valves 8, manifold 7 and line 17 are connected to this modified end compartment in a manner similar to that shown for FIGS. 1 and 2. FIG. 10 is a schematic diagram showing the use of the modified reactor 1' which carries the modified end compartment.

In FIGS. 1 and 10 the reactors 1 and 1' are shown connected to various lines and to the reservoirs 6.

Valves 8 are provided in bottom lines 27 for each of the end compartments as well as in a line 49 in the bottom of the middle compartment which permits draining of the middle compartment over drain line 19. Drain line 19 is also isolated from the manifold 7 by a further valve 8. In the embodiment of FIG. 1, flowmeters 9 are provided in lines 16 and 17. Servovalves 10 are also provided in these lines and are connected to a 4-way valve 11 which receives fluid from top tube 26 of either end compartment 3,3.

A 3-way valve 12 is connected between lines 17 and 18 and drain line 19. Line 17 is the spent fluid line while line 18 is the spent fluid recycle line. A valve 8 is also shown in line 21 which separates degasser drain 21 from drain 19.

The embodiment of FIG. 10 differs from the embodiment of FIG. 1 in that only the end compartments 3 is connected directly to the reservoir 6 over unspent fluid recycle line 16. Flowmeters 9 and servovalves 10 are still however, provided in lines 16 and 17.

FIG. 3 shows the middle compartment 4 which can be supported on downwardly extending supports 50 which are attached to the middle compartment for the purpose of raising the middle compartment off the ground. A pressure transducer 5 is provided near the middle of the middle compartment. A shaft 46 extends upwardly into the bottom of compartment 4 and through a stuffing box or sealing housing 48 where mechanical seal is established around shaft 46 to prevent leakage of fluid out of the bottom of compartment 4. An end plate 47 closes the end of stuffing box 48 and shaft 46 extends through end plate 47 and upwardly almost to the top of the middle compartment 4.

Screw rods 60 hold plate 47 to stuffing box 48 and stuffing box 48 to compartment 4.

A propeller or propellers 54 are connected to shaft 46 inside the compartment 4. Aerator 55 (shown to the side in FIG. 3) is supported horizontally in the lower zone of compartment 4. A gas connection is established through gas entry port 62 with the aerator 55. A large viewing port 59 is also provided which is covered with glass or other transparent material to provide an unobstructed view to the interior of compartment 4. The propellers 54 may be placed anywhere along the shaft 46 depending on the application for the bioreactor. One useful configuration is to place one propeller near the bottom of compartment 4. Another is to use two propellers, one near the top and one near the bottom.

Sampling port 56 is also provided which is normally capped but can be opened to tap a sample of fluid from the compartment 4. It is noted that an RTD input 83 is also provided for the middle compartment. An internal temperature control coil 53 is provided inside compartment 4 for heating purposes. Its terminals can be connected through openings 61 near the top and bottom of compartment 4.

A hollow reducer 58 connects an upper relatively large hole at the top of compartment 4 to the tube 34 which supplies gas and fluid to the hollow hydrophobic tube 39. Reducer 58 focuses the gases from compartment 4 to degasser unit 2.

A seeding tube 51 carries a valve 8 and is provided through the top of compartment 4 for adding biocatalyst to the middle compartment. The degasser recycle line 23 is also connected near the top of compartment 4.

Figure 1A:
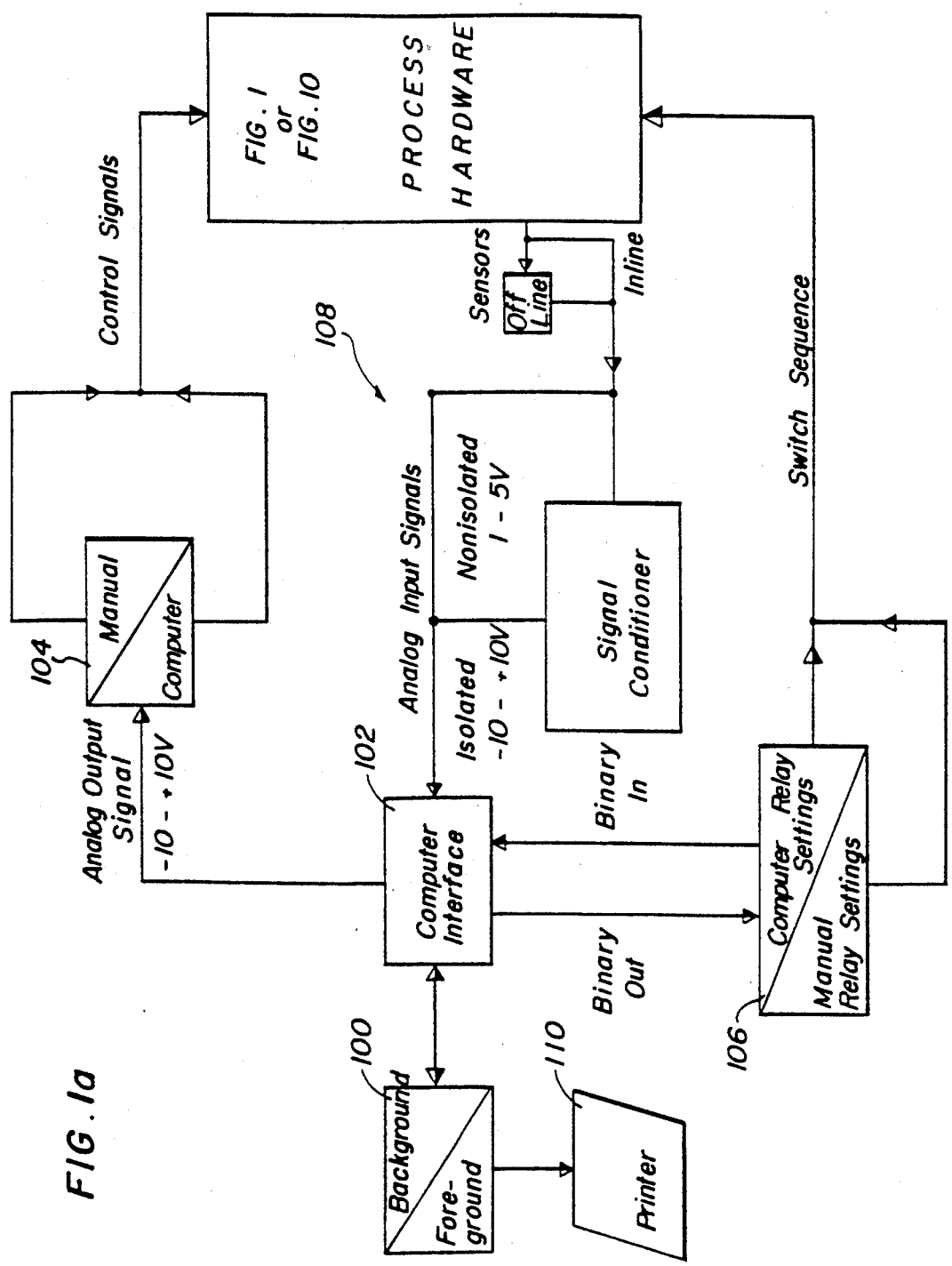
FIG. 1a is a schematic diagram of the microprocessor control for the fluid circuit of FIG. 1.

Referring now to FIG. 1a, a computer or microprocessor 100 is connected to a computer interface 102 for receiving and transmitting analog and digital signals to and from the process hardware which is illustrated in FIGS. 1 or 10. A manually operable switch 104 is connected between the computer interface 102 and the process hardware for selecting whether manually input signals or computer generated signals are to be supplied to the process hardware.

A manually operated switch 106 operates in an analogous way to switch 104 but for the binary signals.

An analog input signal arrangement 108 receives analog sensor signals from the process hardware and supplies them, either directly or after they have been conditioned, to the computer interface 102.

Computer or microprocessor 100 is also connected to a display output 110 which can be a printer or any other conventional display device.

The digital signals from computer interface 102 are supplied to valves 8. At the same time a binary in-signal is fed back to the computer interface so that the computer knows the position for each of the valves 8.

The analog control signals are connected to the servovalves, the pump and the mixing motor for controlling these elements. An analog signal is also connected to the heaters for controlling the heating effect in the middle compartment 4 and in the reservoir 6.

Analog sensor signals are provided from the pressure sensors 5, temperature sensors and the flowmeters 9. Sensor signals also emanate from the servovavles 10 to indicate their position to the computer.

The system is completely automated and operates in the following manner. Utilizing the microprocessor for controlling the operation of the system, the user would initially instruct the microprocesor/controller that he wishes to first sterilize the system before filling the system with media, seeding the middle compartment 4, and then running the system. A microprocessor is used to monitor and/or control the pressure, temperature, flow, pump speeds, mixing rate, sampling, temperature, abration, other internal environmental parameters, valve positions and media reutilization. The microprocessor then reconfigures the system by adjusting all appropriate valves 8 for sterilization and continues to monitor the entire system status during sterilization. Once sterilization has been completed, the microprocessor returns all the valves to their presterilization position, which also configures the system to its original configuration prior to sterilization. Next, the user must fill the system with appropriate media for his application, this is accomplished by aseptically connecting a pump (not shown) and associated tubing to line 71 of the primary reservoir 6 for the purpose of filling the reservoir 6 with sterile media. This pump is plugged into an outlet that is controlled by level controller 64. Once the correct media level has been obtained, the level controller 64 shuts off the electricity to the pump so that no further media may enter the reservoir and permits pump 15 to be activated as well as the temperature control coil 68 in the reservoir. Next, the user instructs the microprocessor to fill the system. The microprocessor configures the system by adjusting all appropriate valves 8 in the manifold 7 as well as the valve and servovalves associated with lines 16, 17, 18 and 21 for the intended purpose. Next, microprocessor activates the pump 15 and fluid travels through the manifold 7, from the reservoir 6 and into each of the bottom tubes 27 and 49 connected to each compartment of the bioreactor. The microprocessor monitors the pressure in the middle compartment 4 until a preset pressure is obtained, signaling that the entire system is filled with media including the degassing unit 2, and all tubes. The microprocessor then shuts-down the pump 15 and reconfigures the system by resetting the valves for the appropriate mode of production selected by the operator. The system can be configured, by having the microprocessor adjust the appropriate valves 8, to run the system in batch, fed-batch, recycle or continuous mode production, and the mode of production can be quickly and easily altered without any effect to the biocatalyst at any time the user desires to make such an alteration to the system.

Next, the biocatalyst must be aseptically added to the middle compartment 4 which occurs through line 51 once the temperature and other environmental conditions have been inputed by the user into the microprocessor where these variables are monitored and controlled by the microprocessor. To seed the middle compartment 4 with the biocatalyst, the pump 15 is reversed and the microprocessor closes all valves 8 except for one valve 8 in line 27 of one end compartment 3. The seeding vessel (not shown) containing the biocatalyst has been aseptically attached to line 51 by the user. On the user's signal, the microprocessor activates the pump 15 and creates a vacuum in the system. Once a preset vacuum has been observed by the microprocessor the valve on the seeding line 51 is opened to pull the biocatalyst into the middle compartment 4. The user signals the microprocesor that the seeding vessel is empty and the microprocessor turns off the pump 15 and reconfigures the system by adjusting the valves 8 back to the previously selected mode of operation. At this point, the microprocessor begins running the system under the specified mode of production. In spite of the mode of production, the biocatalyst is held within the middle compartment 4 by the membranes, and direct microprocessor controlled aeration and agitation of the biocatalyst occurs if desired by the user.

If the system is run in either the batch or fed-batch mode of production, the microprocessor closes all liquid lines runing into or out of the bioreactor, except for sampling port 62 and gas port 56, but may open appropriate valves to perform fed-batch. The microprocessor continues to monitor and control the environmental variables as prescribed by the user as well as agitation and aeration. These will be discussed more fully later in connection with FIGS. 13 and 14.

In continuous or recycle operation of the system, of FIG. 1 liquid is recycled from the reservoir 6 into one of reactor's end compartments 3 using valve 11, within which a vortex is generated for providing tangential motion along the membrane to keep it from being fouled, and wherein a sufficient pressure is generated by servovalve 10 in line 16 to drive the liquid through the membrane packet 20 and into the middle compartment 4 and then through the other membrane packet 20 and finally, the liquid enters into the opposite end compartment 3. In reactor 1' of FIG. 10 the media for generating the pressure to run the system continuously is directed only into end compartment 3. The membranes are of such pore size that the biocatalyst cannot pass through them, however, the user may wish to use whatever pore size that best suits his application. The flow through the end compartment 3 used to create the pressure is measured by the flowmeter 9 in line 16 and controlled by the pump 15 speed and servovalve 10 in line 16 then returns to the reservoir 6. This is done so that the media in the reservoir 6 can be mixed, conditioned to user's specifications, utilize diffusion of oxygen across membrane, and for creating the pressure in the compartment.

Figure 14:
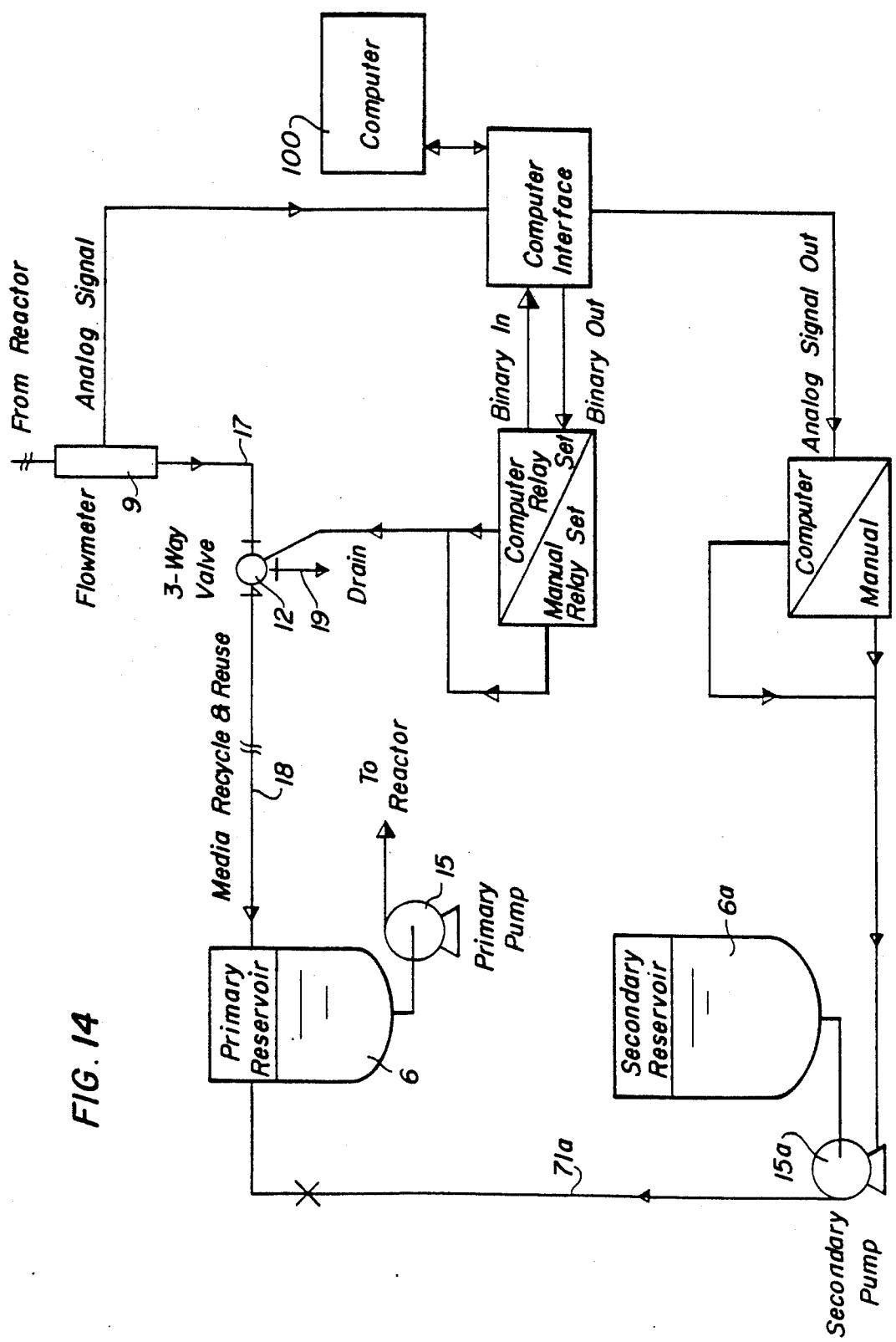
FIG. 14 is a schematic block diagram showing a media recycle and reutilization control system.

If the system is run in recycle or continuous mode production, the user must specify the rate of flow through the entire reactor, (i.e. flowmeter 9, line 17), the environmental and temperature conditions to be maintained inside the reservoir 6. A feedback loop between the flowmeter 9, line 17, and the pump 15 and servovalves 10 permits the microprocessor to monitor and control the flow rate through the reactors 1 and 1' by adjusting servovalve 10, line 16 (coarse control), pump 15 speed, and servovalve 10, line 17 (fine control) until the setpoint value is reached. In the recycle mode, the microprocessor permits the media to return to the reservoir 6 from line 17 to line 18 through the three-way valve 12 (FIG. 14). The returning or spent media is then reconditioned in the reservoir 6 since the microprocessor is controlling the environmental parameters inside the reservoir 6. In the continuous mode, any percentage selected by the user and inputted into the microprocessor, of spent media may be sent down the drain 19 with the remaining amount returned to the reservoir 6 and thus, reutilizing spent media. This reutilization aspect of the system is very important since it permits the user to dilute out the media he is currently using at whatever rate he desires to be replaced by the secondary reservoir 6a which holds another media formulation. The lost media is made-up from the secondary reservoir 6a into the primary reservoir 6 under microprocessor control of a secondary pump 15a through a line 71a.

With reactor 1', in FIG. 10 membrane packet 20 between the intermediate compartment 24 and the modified end compartment 25 may utilize an ultrafilter (Celgard from Celanese Corp.) for the purpose of concentrating the product inside the reactor under continuous operation. Under recycle conditions, the valve 8 in line 26 of the modified end compartment 25 is closed and the valve in line 26 of the intermediate compartment 24 is opened so that none of the spent media is sent through the ultrafilter. The reutilization capability, illustrated in FIG. 14, permits the user to initially grow his biocatalyst up to high densities using a rich media and then permits him the capability of diluting out the rich media at whatever rate he desires and replace the rich media with an inexpensive production media.

With time, fouling of the membrane as the liquid passes out through the middle compartment 4 during continuous operation does occur, however, the microprocessor continuously monitors the pressure in each compartment and when a preset pressure difference is observed between two compartments, the microprocessor reconfigures the system by adjusting the appropriate valving to backwash the fouled membrane as well as pump 15's flow rate. This is done by pumping media into the bottom line 27 of the compartment that comes after the fouled membrane and closing the valve on line 26 of that same compartment (middle compartment 4 excluded). The servovalve in line 16 is left open and a pressure equal to or greater than the measured pressure in this compartment is applied by pump 15 to the inside of this compartment for a preset time. Then the microprocessor reconfigures the system back to its original purpose.

This backwashing capability is used for product collection in reactor 1'. When the pressure difference between the intermediate compartment 24 and the modified end compartment 25 reaches a preset value the microprocessor reconfigures the system by adjusting appropriate valves 8 and backwashes the membrane packet 20 between these two compartments by redirecting the flow in the manifold 7 into the bottom tube 27 of the modified end compartment 25, where a vortex and pressure is generated since the valve 8 in line 26 of the modified end compartment 25 is open and servovalve 10, in line 17 is only partially opened. All other valves 8 and servovalves 10 are closed. Once the pressure inside the modified end compartment 25 has reached the backpressure value of the intermediate compartment 24, the microprocessor opens a valve (not shown) attached to line 27 intermediate compartment 24 before the valve 8 attached to the manifold 7, which sends the product into a sterile collection container (not shown). After a preset time, the microprocessor stops this procedure and reconfigures the system in to its user selected production mode.

Figure 13:
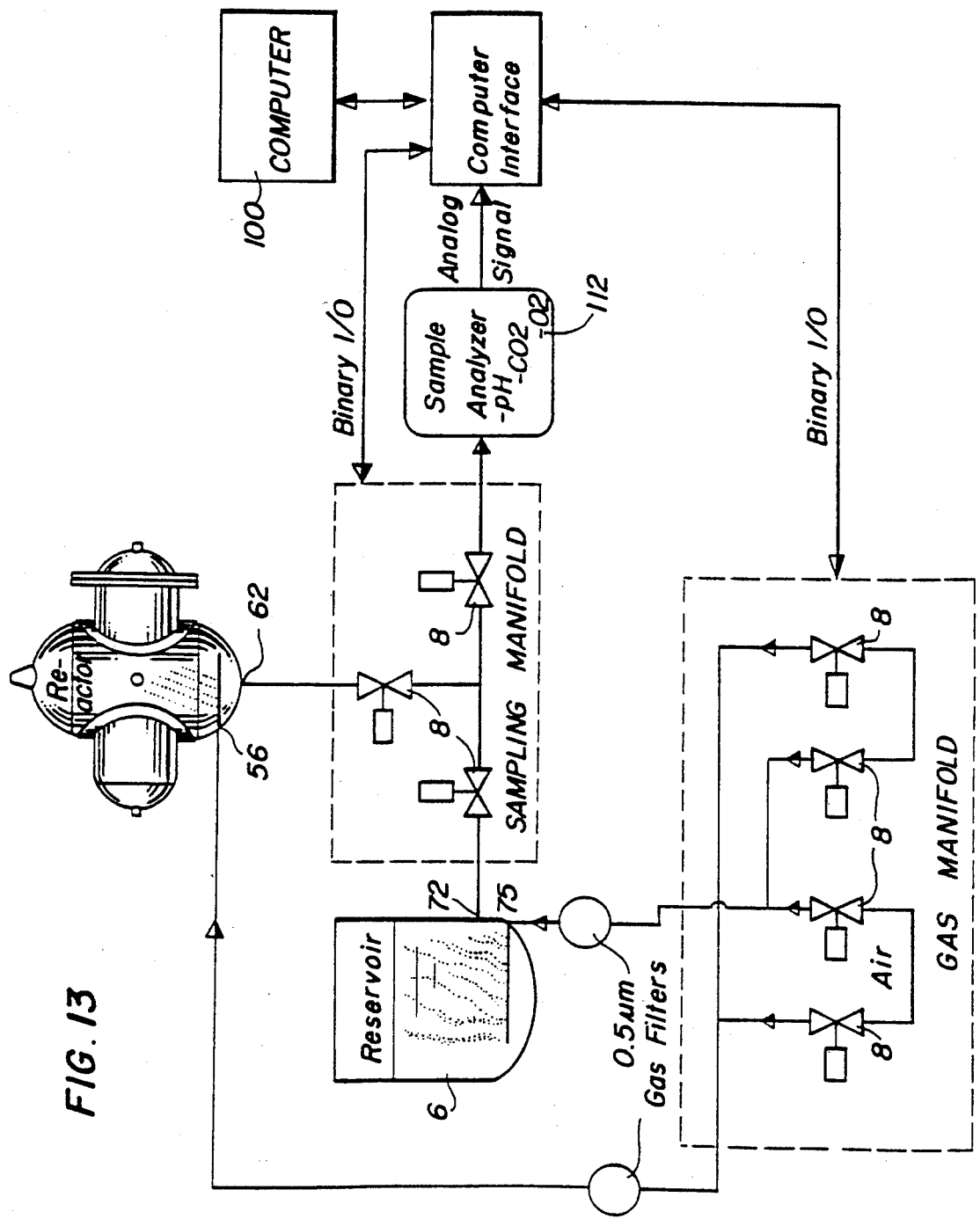
FIG. 13 is a schematic block diagram showing an arrangement for sampling and modifying environmental variables within the bioreactor and the reservoir.

The environmental variables of the reactor 1,1' and the reservoir 6 are monitored off-line through ports 62 and 72 respectively (FIG. 13). The microprocessor 100 opens sampling valves 8 which lead to a sample analyzer 112 whose signals are sent back to the microprocessor. After each sampling, the sample analyzer is washed through automatically to clean away any built-up contamination. Since continuous processes may run for months, sensors that are in-line typically become contaminated with proteins and other materials. These sensors are used to control the environmental conditions inside the system. As the sensors become more contaminated they produce an ever greater error in their reading, which transmits these errors to the microprocessor, which then uses the values to regulate the environmental conditions inside the system. In-line sensor measurement error does not permit the optimal regulation of the environmental conditions for the biocatalyst.

To monitor environmental variables i.e. pH, $CO_2$, $O_2$, the system utilizes an off-line analyzer or sampler 112, which withdraws a sample from the reactor for analysis. Once the sample has been analyzed, the analyzer sensors or probes are then washed with a saline rinse to remove any protein built-up on the sensors or probes. The anayzer is completely automated with sampling frequency and other parameters which may be altered through the microprocessor 100.

A desired pressure level is maintained in one of the end compartments by regulating the degree of opening of servovalve 10. The pressure applied to that compartment when its valve 8 in its line 27 is opened, by pump 15, is then resisted by the partially closed servovalve 10 to produce an excess pressure in the end compartment.

It is noted that two examples of the semipermeable membrane inside the reactor are polypropyleene and polyvinylideene. It is further noted that to provide an efficient and rapid degassing of the middle compartment, a substantial length of hydrophobic membrane tube 39 is used. In an operating example of the invention, eight feet of the tubing are provided in the degasser cylinder 37.

While specific embodiments of the invention have been shown and described in detail to illustrate the application of the principles of the invention, it will be understood that the invention may be embodied otherwise without departing from such principles.

What is claimed is:

1. A biochemical reactor for producing a product from a substrate, comprising:
   a substrate delivery compartment constructed and arranged so as to supply a substrate solution containing a raw material that is to be processed, said substrate delivery compartment including a substrate influent line and a substrate effluent line and a substrate delivery compartment opening;
   a product compartment including an effluent line and a product compartment opening;
   culture formation compartment means including a compartment having a first opening, a second opening, a first semi-permeable membrane extending across said first opening and second a semi-permeable membrane extending across said second opening, said culture formation compartment means being connected to said substrate compartment at said substrate delivery compartment opening, said first semi-permeable membrane separating said substrate delivery compartment opening and said first opening, said culture formation compartment means being connected to said product compartment of said product compartment opening, said second semi-permeable membrane separating said second opening and said product opening, said culture formation compartment means for supporting the growth and formation of an organism to attain a substantially stable biocatalyst which is maintained in said culture formation chamber;
   over-pressure means associated with said substrate chamber effluent line for raising a fluid pressure level in said substrate chamber for urging said substrate solution through each of said first permeable membrane and said second permeable membrane for treating said substrate solution with said biocatalyst for production of a product; and
   mixing means positioned in a bottom portion of said culture formation compartment for mixing contents of said culture formation compartment.

2. A biochemical reactor according to claim 1, wherein:
   said over-pressure means includes restriction means in said substrate chamber effluent line.

3. A bioreactor according to claim 1 further comprising:

supply means including a tube connected to each compartment for supplying and draining fluid to and from each compartment.

4. A bioreactor according to claim 1, further comprising:
   degassing means connected to a top portion of said culture formation compartment for removing gas therefrom.

5. A method of producing a product from a substrate comprising: providing a reactor having a substrate compartment, a formation compartment and a product compartment with a first semi-permeable membrane separating the substrate compartment from the formation compartment and a second semi-permeable membrane separating the formation compartment from the product compartment;
   supplying a solution of substrate under pressure to the substrate compartment so that substrate passes through the first semi-permeable membrane;
   providing a biocatalyst which comprises at least one of cells, enzymes and a catalyst, in the formation compartment which acts upon the substrate to form the product;
   retaining the biocatalyst in the formation compartment during the formation of the product, the substrate solution being provided under sufficient pressure to cause the product to move through the second semi-permeable membrane into the product compartment;
   removing the product from the product compartment;
   supplying the substrate solution tangentially to the substrate compartment to avoid deposition of a solute from the solution on the first semi-permeable membrane; and
   discharging an amount of substrate solution from the substrate compartment at a rate to establish an over-pressure in the substrate compartment above a pressure in the formation compartment and the product compartment.

* * * * *